US009629700B2

(12) United States Patent
Okamura et al.

(10) Patent No.: US 9,629,700 B2
(45) Date of Patent: Apr. 25, 2017

(54) TOOTH CLEANING ASSEMBLY

(71) Applicants: David Okamura, North York (CA); Ghislaine Okamura, North York (CA)

(72) Inventors: David Okamura, North York (CA); Ghislaine Okamura, North York (CA)

( * ) Notice: Subject to any disclaimer, the term of this patent is extended or adjusted under 35 U.S.C. 154(b) by 0 days.

(21) Appl. No.: 14/482,501

(22) Filed: Sep. 10, 2014

(65) Prior Publication Data
US 2016/0067024 A1    Mar. 10, 2016

(51) Int. Cl.
A46B 13/02    (2006.01)
A46B 15/00    (2006.01)
A61C 17/26    (2006.01)

(52) U.S. Cl.
CPC .............. *A61C 17/26* (2013.01); *A46B 13/02* (2013.01); *A46B 15/0085* (2013.01)

(58) Field of Classification Search
CPC ...... A46B 13/02; A46B 15/0085; A61C 17/26
See application file for complete search history.

(56) References Cited

U.S. PATENT DOCUMENTS

| | | | | |
|---|---|---|---|---|
| 2,259,964 A * | 10/1941 | Sussman | ............................ | 15/23 |
| 3,978,852 A * | 9/1976 | Annoni | .......................... | 601/142 |
| 4,156,620 A * | 5/1979 | Clemens | ............................ | 134/6 |
| 5,000,684 A * | 3/1991 | Odrich | ..................... | A61C 15/00 |
| | | | | 15/22.1 |
| 5,071,348 A * | 12/1991 | Woog | ...................... | A61C 17/26 |
| | | | | 132/308 |
| 5,099,536 A | 3/1992 | Hirabayashi | | |
| 5,224,231 A * | 7/1993 | Nacar | ............................ | 15/22.2 |
| 5,269,104 A * | 12/1993 | DiBiagio | ........................ | 451/344 |
| 5,273,428 A * | 12/1993 | Fischer | ........................... | 433/80 |
| 6,295,681 B1 * | 10/2001 | Dolah | ............................ | 15/22.1 |
| 6,442,785 B1 * | 9/2002 | Robinson | ............... | A46B 9/028 |
| | | | | 15/167.1 |
| D648,539 S | 11/2011 | Wai | | |
| 8,677,542 B1 * | 3/2014 | Whillock | ....................... | 15/22.1 |
| 2004/0117930 A1 * | 6/2004 | Townley et al. | .................. | 15/28 |
| 2005/0271997 A1 | 12/2005 | Mikami et al. | | |
| 2006/0096053 A1 * | 5/2006 | Fischer et al. | ............... | 15/167.1 |
| 2007/0124877 A1 * | 6/2007 | Lee | ................................ | 15/22.1 |
| 2007/0264608 A1 | 11/2007 | Brosnihan | | |
| 2007/0271714 A1 | 11/2007 | Adam et al. | | |
| 2009/0029323 A1 * | 1/2009 | Nejat | ............................ | 433/216 |
| 2009/0148808 A1 | 6/2009 | Alexander et al. | | |
| 2011/0099739 A1 | 5/2011 | Whillock | | |
| 2012/0021382 A1 * | 1/2012 | Dickie | ................. | A61C 15/047 |
| | | | | 433/216 |
| 2012/0258418 A1 | 10/2012 | Shen | | |

FOREIGN PATENT DOCUMENTS

NL          9002185    *  5/1992
WO     WO2007109136       9/2007

* cited by examiner

*Primary Examiner* — Randall Chin

(57) ABSTRACT

A tooth cleaning assembly for removing embedded plaque between a user's tooth and gum includes a housing that may be gripped by the user. A motor is coupled to the housing. A shaft is coupled to the motor. The motor rotates the shaft. A brush is structured to taper to a point. The brush may be positionable between the user's tooth and the user's gum. The brush removes embedded plaque. The brush is mechanically coupled to the shaft so the shaft rotates the brush. An actuator is coupled to the housing. The actuator is electrically coupled to the motor. The actuator actuates and de-actuates the motor.

8 Claims, 4 Drawing Sheets

TOOTH CLEANING ASSEMBLY

BACKGROUND OF THE DISCLOSURE

Field of the Disclosure

The disclosure relates to cleaning devices and more particularly pertains to a new cleaning device for removing embedded plaque between a user's tooth and gum.

SUMMARY OF THE DISCLOSURE

An embodiment of the disclosure meets the needs presented above by generally comprising a housing that may be gripped by a user. A motor is coupled to the housing. A shaft is coupled to the motor. The motor rotates the shaft. A brush is structured to taper to a point. The brush may be positionable between a user's tooth and the user's gum. The brush removes embedded plaque. The brush is mechanically coupled to the shaft so the shaft rotates the brush. An actuator is coupled to the housing. The actuator is electrically coupled to the motor. The actuator actuates and de-actuates the motor.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
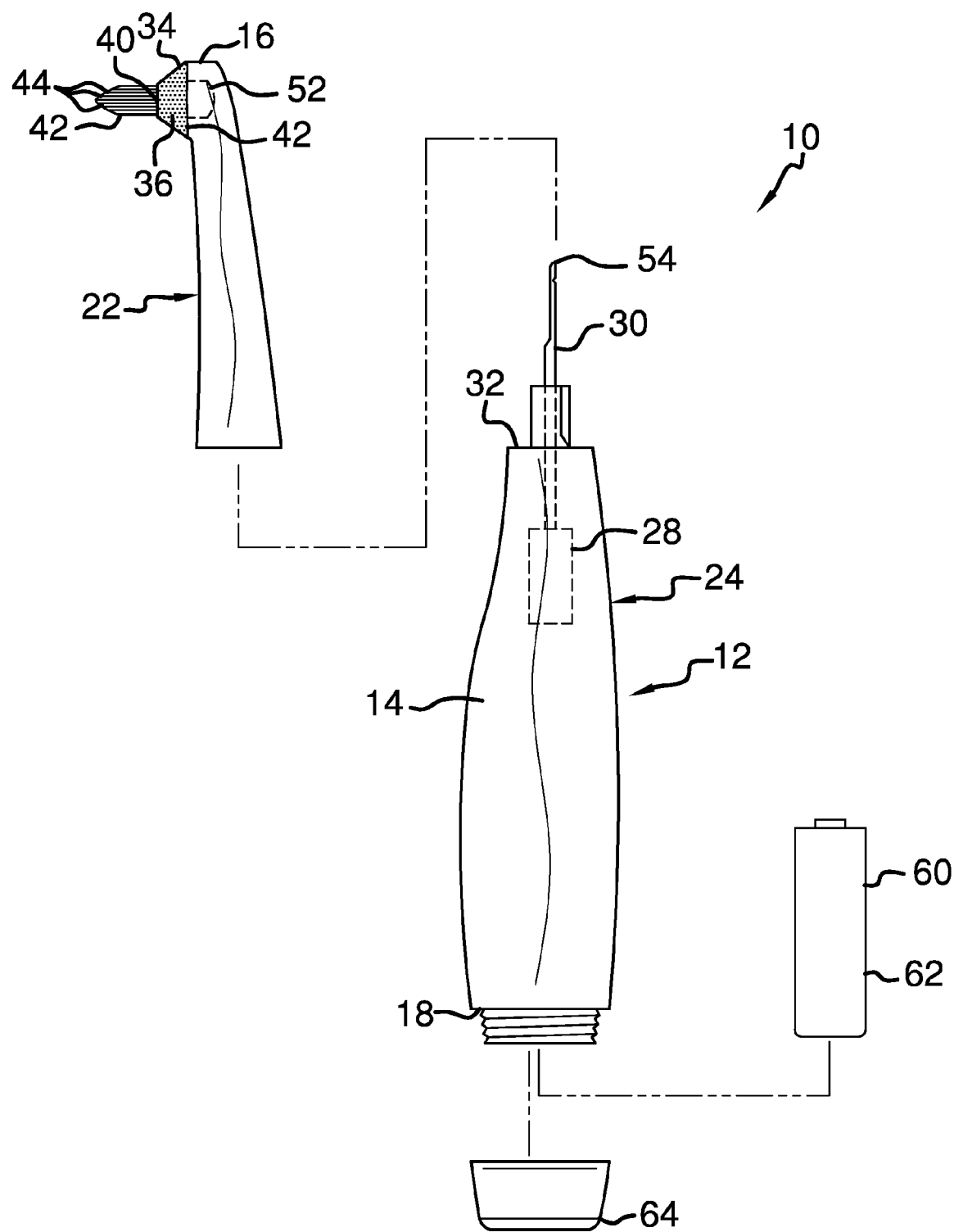
FIG. 1 is an exploded left side view of a tooth cleaning assembly according to an embodiment of the disclosure.
Figure 2:
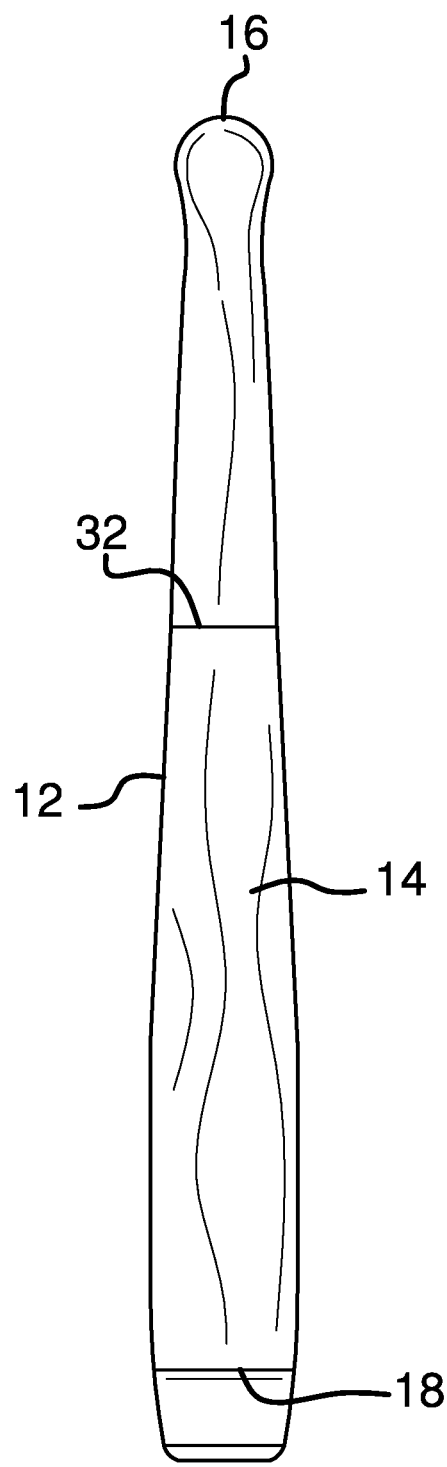
FIG. 2 is a back view of an embodiment of the disclosure.
Figure 3:
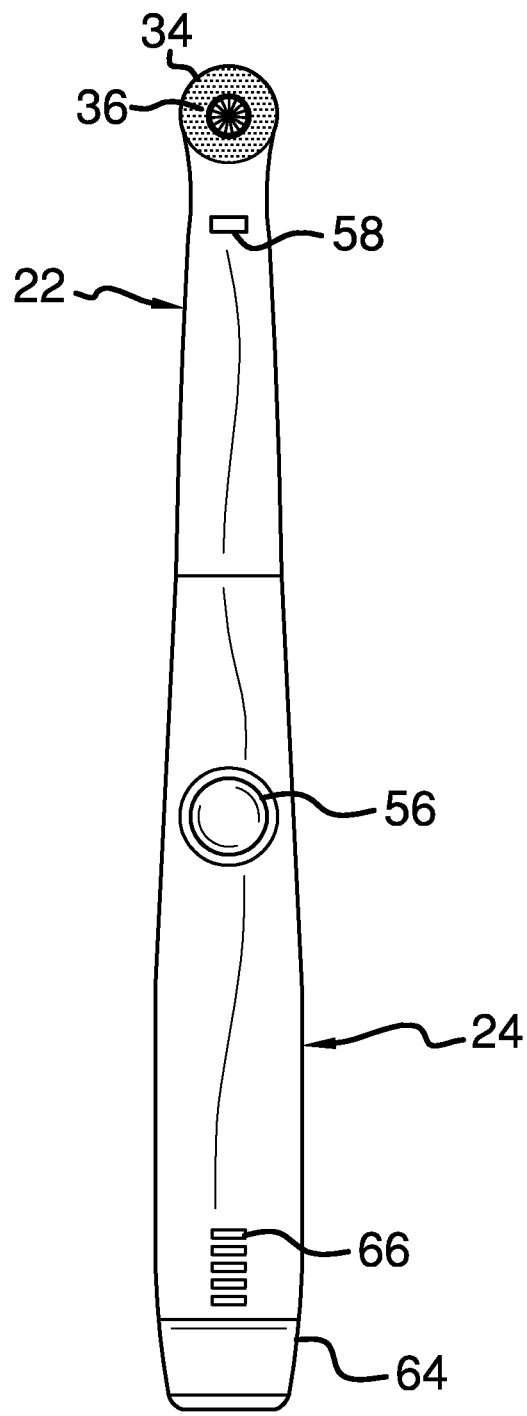
FIG. 3 is a front view of an embodiment of the disclosure.
Figure 4:
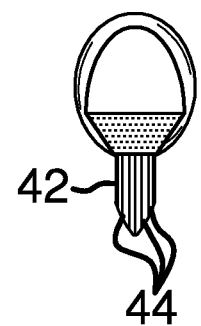
FIG. 4 is a top view of an embodiment of the disclosure.
Figure 5:
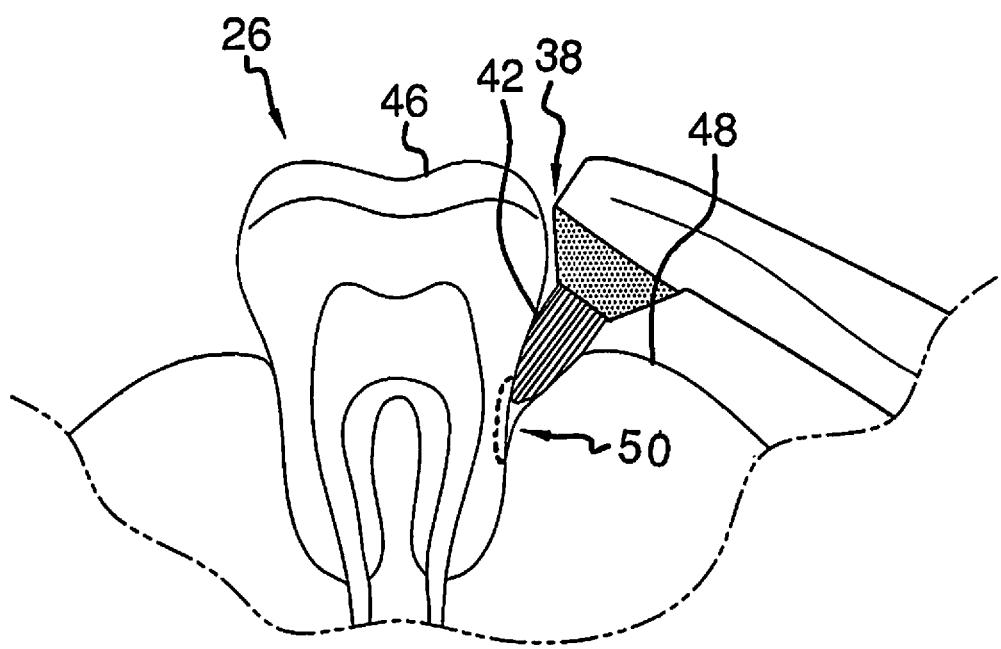
FIG. 5 is an in-use view of an embodiment of the disclosure.

With reference now to the drawings, and in particular to FIGS. 1 through 5 thereof, a new cleaning device embodying the principles and concepts of an embodiment of the disclosure and generally designated by the reference numeral 10 will be described.

As best illustrated in FIGS. 1 through 5, the tooth cleaning assembly 10 generally comprises a housing 12. The housing 12 has an outer wall 14 extending between a top end 16 and a bottom end 18 of the housing 12. The outer wall 14 of the housing 12 is structured to define a top portion 22 of the housing 12 removably coupled to a bottom portion 24 of the housing 12. The bottom portion 24 of the housing 12 may be gripped by a user 26.

A motor 28 is coupled to the housing 12. The motor 28 is positioned within the bottom portion 24 of the housing 12. The motor 28 may be an electrical motor of any conventional design.

A shaft 30 is coupled to the motor 28. The shaft 30 extends outwardly from an upper end 32 of the bottom portion 24 of the housing 12. The motor 28 rotates the shaft 30.

A cowl 34 is provided coupled to the top portion 22. The cowl 34 has an outermost wall 36 extending between each of a front end 40 and a back end 38 of the cowl 34. The outermost wall 36 of the cowl 34 tapers between the back 38 and front 40 ends of the cowl 34. The outermost wall 36 of the cowl 34 has a color that is distinct from a color of the outer wall 14 of the housing 12. The color of the cowl 34 is distinct particularly from a color of the top portion 22 of the housing 12. The top portion 22 of the housing 12 may be replaceable and the housing 12 may be provided with a plurality of top portions 22 allowing individual users to utilize the assembly 10 with each top portion 22 used only by a single user. The color of the cowl 34 of each top portion 22 may be distinct to facilitate identification of each top portion 22 preventing two persons from using the same top portion 22.

The back end 38 of the cowl 34 is coupled to the outer wall 14 of the top portion 22 of the housing 12. The front end 40 of the cowl 34 is directed laterally away from the outer wall 14 of the housing 12. Additionally, the cowl 34 is positioned adjacent to the top end 16 of the housing 12.

A brush 42 is provided. The brush 42 comprises a plurality of bristles 44 each coupled to and extending laterally away from the front end 40 of the cowl 34. The bristles 44 are arranged forming a cylindrical shape having a distal portion relative to the cowl 34. The distal portion tapers extending away from the cowl 34 to define a point. The brush 42 may be positioned between a user's tooth 46 and the user's gum 48. The brush 42 removes embedded plaque 50 that would otherwise remain between the user's tooth 46 and gum 48.

A drive 52 is provided. The drive 52 is coupled to the top portion 22 of the housing 12. Moreover, the drive 52 is positioned within an interior of the top portion 22 of the housing 12. The drive 52 engages the brush 42. The drive 52 rotates the brush 42. The drive 52 may be a gear drive of any conventional design. A free end 54 of the shaft 30 engages the drive 52 when the top portion 22 of the housing 12 is coupled to the bottom portion 24 of the housing 12. The shaft 30 rotates the drive 52.

An actuator 56 is coupled to the outer wall 14 of the bottom portion 24 of the housing 12. The actuator 56 is electrically coupled to the motor 28. The actuator 56 actuates and de-actuates the motor 28. A light emitter 58 is coupled to the outer wall 14 of the top portion 22 of the housing 12. The light emitter 58 is electrically coupled to the actuator 56. Additionally, the light emitter 58 is positioned proximate the cowl 34. The light emitter 58 illuminates the user's tooth 46 and gum 48.

A power supply 60 is coupled to the bottom portion 24 of the housing 12. The power supply 60 is electrically coupled to the actuator 56. The power supply 60 comprises at least one battery 62. A cap 64 threadably engages the bottom end 18 of the bottom portion 24 of the housing 12. The battery 62 is positioned beneath the cap 64.

A charge indicator 66 is coupled to the outer wall 14 of the bottom portion 24 of the housing 12. The charge indicator 66 is positioned proximate the bottom end 18 of the bottom portion 24 of the housing 12. The charge indicator 66 is electrically coupled to the power supply 60. The charge indicator 66 indicates a level of charge of the power supply 60.

In use, the assembly 10 is utilized to remove plaque 50 from between the user's tooth 46 and gum 48. The brush 42 is rotated while the brush 42 is positioned between the user's tooth 46 and gum 48. The rotation of the brush 42 abrades the user's tooth 46 and gum 48.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A tooth cleaning assembly comprising:
a housing configured to be gripped by a user, said housing having an outer wall extending between a top end and a bottom end of said housing, said outer wall of said housing being structured to define a top portion of said housing removably coupled to a bottom portion of said housing;
a motor coupled to said housing;
a shaft coupled to said motor such that said motor rotates said shaft;
a brush structured to taper to a point such that said brush is configured to be positionable between a user's tooth and the user's gum wherein said brush removes embedded plaque, said brush being mechanically coupled to said shaft such that said shaft rotates said brush, said brush comprising a plurality of bristles each being coupled to and extending laterally away from said outer wall of said top portion of said housing, said brush being positioned adjacent to said top end of said housing, said bristles being structured to taper to a point such that said brush is configured to be positionable between a user's tooth and the user's gum wherein said brush removes embedded plaque;
an actuator coupled to said housing, said actuator being electrically coupled to said motor such that said actuator actuates and de-actuates said motor; and
a cowl positioned between said outer wall and said bristles, said bristles extending away from said cowl, said cowl tapering extending laterally away from said top portion of said housing, said cowl having a color wherein said cowl is configured for identifying respective top portions interchangeably couplable to said bottom portion by providing distinct cowl colors for each interchangeable top portion.

2. The assembly according to claim 1, further comprising:
said motor being positioned within said bottom portion of said housing; and
said shaft extending outwardly from an upper end of said bottom portion of said housing.

3. The assembly according to claim 1, further comprising a drive coupled to said top portion of said housing, said drive being positioned within an interior of said top portion of said housing such that said drive engages said brush, said drive selectively rotating said brush.

4. The assembly according to claim 3, further comprising a free end of said shaft engaging said drive when said top portion of said housing is coupled to said bottom portion of said housing such that said shaft rotates said drive.

5. The assembly according to claim 1, further comprising a power supply coupled to said bottom portion of said housing.

6. The assembly according to claim 5, further comprising said power supply being electrically coupled to said actuator.

7. The assembly according to claim 6, further comprising said power supply comprising at least one battery.

8. A tooth cleaning assembly comprising:
a housing, said housing having an outer wall extending between a top end and a bottom end of said housing, said outer wall of said housing being structured to define a top portion of said housing removably coupled to a bottom portion of said housing, said bottom portion of said housing being configured to be gripped by a user;
a motor coupled to said housing wherein said motor is positioned within said bottom portion of said housing;
a shaft coupled to said motor such that said shaft extends outwardly from an upper end of said bottom portion of said housing, said motor rotating said shaft;
a brush, said brush comprising a plurality of bristles each being coupled to and extending laterally away from said outer wall of said top portion of said housing, said brush being positioned adjacent to said top end of said housing, said bristles being structured to taper to a point such that said brush is configured to be positionable between a user's tooth and the user's gum wherein said brush removes embedded plaque;
a cowl coupled to said top portion of said housing, said cowl being positioned between said outer wall and said bristles, said bristles extending away from said cowl, said cowl tapering extending laterally away from said top portion of said housing, said cowl having a color wherein said cowl is configured for identifying respective top portions interchangeably couplable to said bottom portion by providing distinct cowl colors for each interchangeable top portion;
a drive coupled to said top portion of said housing, said drive being positioned within an interior of said top portion of said housing such that said drive engages said brush, said drive selectively rotating said brush;
a free end of said shaft engaging said drive when said top portion of said housing is coupled to said bottom portion of said housing such that said shaft rotates said drive;
an actuator coupled to said housing, said actuator being electrically coupled to said motor such that said actuator actuates and de-actuates said motor; and
a power supply coupled to said bottom portion of said housing, said power supply being electrically coupled to said actuator, said power supply comprising at least one battery.

* * * * *